(12) United States Patent
Taniguchi et al.

(10) Patent No.: US 8,110,597 B2
(45) Date of Patent: Feb. 7, 2012

(54) RADIOACTIVE ISOTOPE-LABELED DYE COMPOUND

(75) Inventors: Masahiko Taniguchi, Kanagawa (JP); Junji Nishigaki, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1231 days.

(21) Appl. No.: 11/925,228

(22) Filed: Oct. 26, 2007

(65) Prior Publication Data
US 2011/0263872 A1    Oct. 27, 2011

(30) Foreign Application Priority Data

Oct. 27, 2006 (JP) ................................ 2006-292446
Oct. 25, 2007 (JP) ................................ 2007-277070

(51) Int. Cl.
*A61K 31/40* (2006.01)
*C07D 209/02* (2006.01)
(52) U.S. Cl. ........................ 514/414; 548/455
(58) Field of Classification Search .................. 548/455; 514/414
See application file for complete search history.

(56) References Cited

U.S. PATENT DOCUMENTS
6,114,350 A * 9/2000 Randall et al. ................ 514/311
* cited by examiner

*Primary Examiner* — Rebecca Anderson
(74) *Attorney, Agent, or Firm* — Sughrue Mion, PLLC

(57) ABSTRACT

A radioactive isotope-labeled dye compound represented by the following general formula (I):

General formula (I)

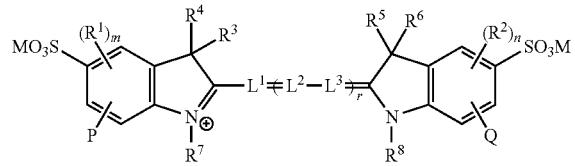

wherein $R^1$ and $R^2$ represent a substituent, $R^3$ to $R^6$ represent a substituted or unsubstituted alkyl group; $R^7$ and $R^8$ represent a substituted or unsubstituted alkyl group; $L^1$ to $L^3$ represent a substituted or unsubstituted methine group; r represents an integer of 0 to 3; P and Q represent $^{123}I$, $^{124}I$, $^{125}I$, $^{131}I$ or $^{18}F$; M represents hydrogen atom, Na, or K; and m and n represent an integer of 0 to 2.

3 Claims, No Drawings

RADIOACTIVE ISOTOPE-LABELED DYE COMPOUND

CROSS-REFERENCE TO RELATED APPLICATIONS

This application claims benefit of priorities under 35 USC 119 to Japanese Patent Applications No. 2006-292446 filed on Oct. 27, 2006, and No. 2007-277070 filed on Oct. 25, 2007, the disclosures of which are each expressly incorporated by reference herein in their entireties.

BACKGROUND OF THE INVENTION

1. Field of the Invention

The present invention relates to a radioactive isotope-labeled dye compound.

2. Description of the Prior Art

The present invention provides a dye which can be used in the field of marking a substance and identifying the substance, especially for a marking method for maintaining marking for a limited period of time to enable detection. A marking method comprising performing marking with a dye containing a radioisotope of an appropriate life, so that radiation then disappears after a certain period of time to leave a mark similar to those obtained with usual dyes, not only provides visible information, but also enables accurate recording of the mark over time progress, and therefore a wide range of uses thereof can be expected (WO2004/065134, the disclosure of which is expressly incorporated herein by reference in its entirety). Further, the dye can be expected to be used as a radioactive medicament (International Journal of Applied Radiation and Isotopes 34, 1383-1393, (1983), the disclosure of which is expressly incorporated herein by reference in its entirety).

SUMMARY OF THE INVENTION

An object of the present invention is to provide a novel radioactive isotope-labeled dye compound.

The inventors of the present invention conducted various researches, thus found a preparation method enabling efficient preparation of a novel radioactive isotope-labeled dye compound, and accomplished the present invention on the basis of the above finding. The present invention thus provides the following items [1] to [7].

[1] A compound represented by the following general formula (I):

General formula (I)

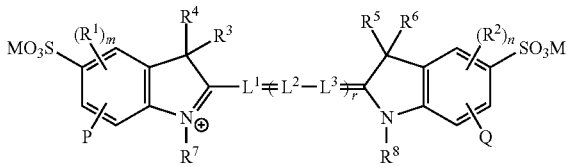

wherein $R^1$ and $R^2$ each independently represent a substituent, $R^3$ to $R^6$ are the same or different, and each represent a substituted or unsubstituted alkyl group; $R^7$ and $R^8$ represent a substituted or unsubstituted alkyl group; $L^1$ to $L^3$ are the same or different, and each represent a substituted or unsubstituted methine group; r represents an integer of 0 to 3; and two or more $L^2$ and $L^3$ existing when r is 2 or larger may be the same or different; P and Q independently represent $^{123}I$, $^{124}I$, $^{125}I$, $^{131}I$ or $^{18}F$; M represents hydrogen atom, Na, or K; and m and n independently represent an integer of 0 to 2.

[2] The compound according to [1], which is represented by the following general formula (II):

General formula (II)

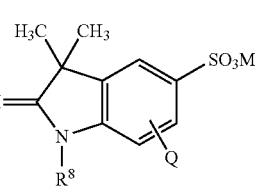

wherein $R^9$ represents hydrogen atom, a substituted or unsubstituted alkyl group, a substituted or unsubstituted aryl group, a substituted or unsubstituted heterocyclic group, a substituted or unsubstituted acylamino group, a substituted or unsubstituted arylamino group, a substituted or unsubstituted arylthio group, a substituted or unsubstituted aryloxy group, a substituted or unsubstituted carbamoyl group or a halogen atom.

[3] A compound represented by any one of the following formulas 1 to 4:

Formula 1

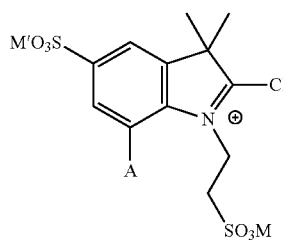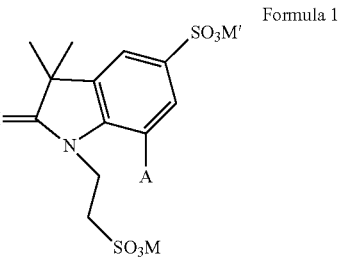

Formula 2

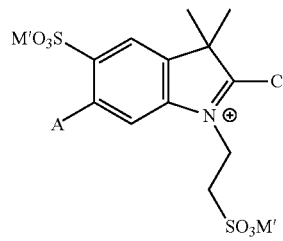 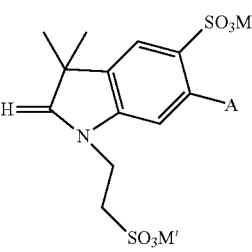

Formula 3

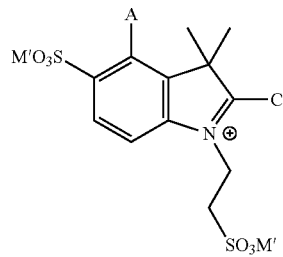 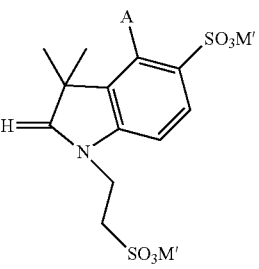

Formula 4

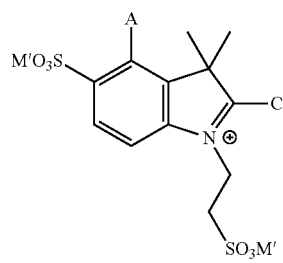 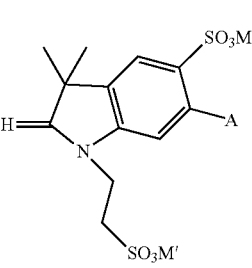

wherein A represents $^{123}$I, $^{124}$I, $^{125}$I, $^{131}$I, or $^{18}$F, and M' represents Na or K.

[4] A compound represented by the following general formula (III):

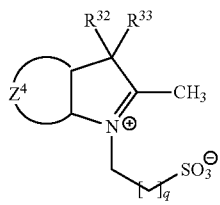

General formula (III)

wherein $R^{32}$ and $R^{33}$ are the same or different, and each represent a substituted or unsubstituted alkyl group, $Z^4$ represents an atomic group forming a condensed benzo ring having one or more substituents selected from the group consisting of $^{123}$I, $^{124}$I, $^{125}$I, $^{131}$I, and $^{18}$F and one or more substituents selected from the group consisting of sulfo group and sulfo group of which hydrogen atom is replaced with an alkali metal, or a condensed naphtho ring having one or more substituents selected from the group consisting of $^{123}$I, $^{124}$I, $^{125}$I, $^{131}$I, and $^{18}$F and one or more substituents selected from the group consisting of sulfo group and sulfo group of which hydrogen atom is replaced with an alkali metal, and q represents an integer of 1 to 5.

[5] A method of preparing a radioactive isotope-labeled dye compound, which comprises the step of reacting the compound represented by the general formula (III) according to [4] and a dianil compound.

[6] A compound represented by the following general formula (IV):

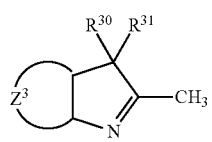

General formula (IV)

wherein $R^{30}$ and $R^{31}$ are the same or different, and each represent a substituted or unsubstituted alkyl group, and $Z^3$ represents an atomic group forming a condensed benzo ring having one or more substituents selected from the group consisting of iodine and fluorine and one or more substituents selected from the group consisting of sulfo group and sulfo group of which hydrogen atom is replaced with an alkali metal, or a condensed naphtho ring having one or more substituents selected from the group consisting of iodine and fluorine and one or more substituents selected from the group consisting of sulfo group and sulfo group of which hydrogen atom is replaced with an alkali metal.

[7] The compound according to [6], which is represented by the following general formula (V):

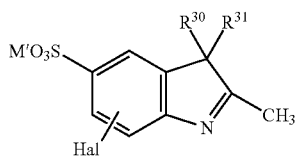

General formula (V)

wherein Hal represents iodine or fluorine, and M' represents hydrogen atom or an alkali metal atom.

DESCRIPTION OF THE PREFERRED EMBODIMENTS

First, the compound represented by the general formula (I) will be explained in detail.

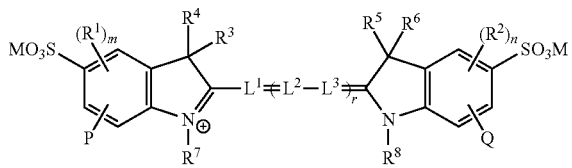

$R^1$ and $R^2$ independently represents a substituent. Examples of the substituent include substituents selected from the following substituent group. Substituent group: a halogen atom, an alkyl group, an alkenyl group, an alkynyl group, an aryl group, a heterocyclic group, cyano group, hydroxyl group, nitro group, carboxyl group, an alkoxyl group, an aryloxy group, a silyloxy group, a heterocyclyloxy group, an acyloxy group, a carbamoyloxy group, an alkoxycarbonyloxy group, an aryloxycarbonyloxy group, amino group, an alkylamino group, an arylamino group, an acylamino group, an aminocarbonylamino group, an alkoxycarbonylamino group, an aryloxycarbonylamino group, a sulfamoylamino group, an alkyl- or aryl-sulfonylamino group, mercapto group, an alkylthio group, an arylthio group, a heterocyclylthio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclylazo group, an imido group, a phosphino group, a phosphinyl group, a phosphinyloxy group, phosphinylamino group, and a silyl group.

Among these groups, those that can form a salt, and those that can form a salt by dissociation of one or more hydrogen ions may be those any of which group or groups form a salt. Examples of counter ion in these salts include positive charge or negative charge existing in the compound of the present invention, an alkali metal ion, and an alkaline earth metal ion.

Examples of the halogen atom include, for example, chlorine atom, bromine atom, and iodine atom. The alkyl group may be a straight, branched or cyclic alkyl group, and examples include a straight alkyl group having 1 to 30 carbon atoms (for example, methyl, ethyl, n-propyl, isopropyl, t-butyl, n-octyl, eicosyl, 2-ethylhexyl), a cycloalkyl group having 3 to 30 carbon atoms (for example, cyclohexyl, cyclopentyl, 4-n-dodecylcyclohexyl), a bicycloalkyl group having 5 to 30 carbon atoms (monovalent group obtained by eliminating one hydrogen atom from a bicycloalkane having 5 to 30 carbon atoms, for example, bicyclo[1,2,2]heptan-2-yl, bicyclo[2,2,2]octan-3-yl), an alkyl group having a tricyclo structure having still more ring systems, and the like.

The alkenyl group may be a straight, branched or cyclic alkenyl group, and examples include a straight alkenyl group having 2 to 30 carbon atoms (for example, vinyl, allyl, prenyl, geranyl, oleoyl), a cycloalkenyl group having 3 to 30 carbon atoms (monovalent group obtained by eliminating one hydrogen atom from a cycloalkene having 3 to 30 carbon atoms, for example, 2-cyclopenten-1-yl, 2-cyclohexen-1-yl), a bicycloalkenyl group having 5 to 30 carbon atoms (monovalent group obtained by eliminating one hydrogen atom from a bicycloalkene having one double bond, for example, bicyclo[2,2,1]hept-2-en-1-yl, bicyclo[2,2,2]oct-2-en-4-yl), and the like. Preferred examples of the alkynyl group include an alkynyl group having 2 to 30 carbon atoms (for example, ethynyl, propargyl). The aryl group may preferably be an aryl group having 6 to 30 carbon atoms, and examples include, for example, phenyl, p-tolyl, and naphthyl.

The heterocyclic group may preferably be a 5- or 6-membered heterocyclic group, and may be a monovalent group obtained by eliminating one hydrogen atom from an aromatic or non-aromatic heterocyclic compound. It is more preferably a 5- or 6-membered aromatic heterocyclic group having 3 to 30 carbon atoms, and examples include, for example, 2-furyl, 2-thienyl, 2-pyrimidinyl, and 2-benzothiazolyl. The alkoxyl group may preferably be an alkoxyl group having 1 to 30 carbon atoms, and examples include, for example, methoxy, ethoxy, isopropoxy, t-butoxy, and n-octyloxy. The aryloxy group may preferably be an aryloxy group having 6 to 30 carbon atoms, and examples include, for example, phenoxy group. The silyloxy group may preferably be a silyloxy group having 3 to 20 carbon atoms, and examples include, for example, trimethylsilyloxy and t-butyldimethylsilyloxy.

The heterocyclyloxy group may preferably be a heterocyclyloxy group having 2 to 30 carbon atoms, and examples include tetrazole-5-oxy and 2-tetrahydropyranyloxy. The acyloxy group may be formyloxy group, an alkylcarbonyloxy group having 2 to 30 carbon atoms, an arylcarbonyloxy group having 6 to 30 carbon atoms, or the like, and examples include, for example, formyloxy, acetyloxy, pivaloyloxy, stearoyloxy, benzoyloxy, and phenylcarbonyloxy. The carbamoyloxy group may preferably be a carbamoyloxy group having 1 to 30 carbon atoms, and examples include, for example, N,N-dimethylcarbamoyloxy, N,N-diethylcarbamoyloxy, morpholinocarbonyloxy, N,N-di-n-octylaminocarbonyloxy, and N-n-octylcarbamoyloxy. The alkoxycarbonyloxy group may preferably be an alkoxycarbonyloxy group having 2 to 30 carbon atoms, and examples include, for example, methoxycarbonyloxy, ethoxycarbonyloxy, t-butoxycarbonyloxy, and n-octylcarbonyloxy.

The aryloxycarbonyloxy group may preferably be an aryloxycarbonyloxy group having 7 to 30 carbon atoms, and examples include, for example, phenoxycarbonyloxy. The alkylamino group may be an alkylamino group having 1 to 30 carbon atoms, and examples include, for example, methylamino and dimethylamino. The arylamino group may preferably be an arylamino group having 6 to 30 carbon atoms, and examples include, for example, an anilino and diphenylamino. The acylamino group may preferably be formylamino group, an alkylcarbonylamino group having 1 to 30 carbon atoms, or an arylcarbonylamino group having 6 to 30 carbon atoms, and examples include, for example, formylamino, acetylamino, pivaloylamino, lauroylamino, benzoylamino, and 3,4,5-tri-n-octyloxyphenylcarbonylamino. The aminocarbonylamino group may preferably be an aminocarbonylamino group having 1 to 30 carbon atoms, and examples include, for example, carbamoylamino, N,N-dimethylaminocarbonylamino, N,N-diethylaminocarbonylamino, and morpholinocarbonylamino.

The alkoxycarbonylamino group may preferably be an alkoxycarbonylamino group having 2 to 30 carbon atoms, and examples include, for example, methoxycarbonylamino, ethoxycarbonylamino, t-butoxycarbonylamino, and n-octadecyloxycarbonylamino. The aryloxycarbonylamino group may preferably be an aryloxycarbonylamino group having 7 to 30 carbon atoms, and examples include, for example, phenoxycarbonylamino. The sulfamoylamino group may preferably be a sulfamoyl amino group having 0 to 30 carbon atoms, and examples include, for example, sulfamoylamino, N,N-dimethylaminosulfonylamino, and N-n-octylaminosulfonylamino. The alkyl- or aryl-sulfonylamino group may preferably be an alkylsulfonylamino having 1 to 30 carbon atoms or an arylsulfonylamino having 6 to 30 carbon atoms, and examples include, for example, methylsulfonylamino, butylsulfonylamino, and phenylsulfonylamino. The alkylthio group may preferably be an alkylthio group having 1 to 30 carbon atoms, and examples include, for example, methylthio, ethylthio, and n-hexadecylthio. The arylthio group may preferably be an arylthio group having 6 to 30 carbon atoms, and examples include, for example, phenylthio. The heterocyclylthio group may preferably be a heterocyclylthio group having 2 to 30 carbon atoms, and examples include, for example, 2-benzothiazolylthio and tetrazol-5-ylthio.

The sulfamoyl group may preferably be a substituted or unsubstituted sulfamoyl group having 0 to 30 carbon atoms, and examples include, for example, N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl. The alkylsulfinyl group and arylsulfinyl group may preferably be an alkylsulfinyl group having 1 to 30 carbon atoms and an arylsulfinyl group having 6 to 30 carbon atoms, respectively, and examples include, for example, methylsulfinyl, ethylsulfinyl, and phenylsulfinyl. The alkyl- or aryl-sulfonyl group may preferably be an alkylsulfonyl group having 1 to 30 carbon atoms or an arylsulfonyl group having 6 to 30 carbon atoms, and examples include, for example, methylsulfonyl, ethylsulfonyl, and phenylsulfonyl. The acyl group may preferably be formyl group, an alkylcarbonyl group having 2 to 30 carbon atoms, an arylcarbonyl group having 7 to 30 carbon atoms, or a heterocyclylcarbonyl group having 4 to 30 carbon atoms in which a carbon atom of the heterocyclic group binds to the carbonyl group, and examples include, for example, acetyl, pivaloyl, stearoyl, benzoyl, 2-pyridylcarbonyl, and 2-furylcarbonyl. The aryloxycarbonyl group may preferably be an aryloxycarbonyl group having 7 to 30 carbon atoms, and examples include, for example, phenoxycarbonyl.

The alkoxycarbonyl group may preferably be an alkoxycarbonyl group having 2 to 30 carbon atoms, and examples include, for example, methoxycarbonyl, ethoxycarbonyl, t-butoxycarbonyl, and n-octadecyloxycarbonyl. The carbamoyl group may preferably be a carbamoyl group having 1 to 30 carbon atoms, and examples include, for example, carbamoyl, N-methylcarbamoyl, N,N-dimethylcarbamoyl, N,N-di-n-octylcarbamoyl, and N-(methylsulfonyl)carbamoyl. The arylazo group and heterocyclylazo group may preferably be an arylazo group having 6 to 30 carbon atoms and a heterocyclylazo group having 3 to 30 carbon atoms, respectively, and examples include, for example, phenylazo, and 1,3,4-thiadiazol-2-ylazo. Preferred examples of the imido group include N-succinimido and N-phthalimido. The phosphino group may preferably be a phosphino group having 2 to 30 carbon atoms, and examples include, for example, dimethylphosphino, diphenylphosphino, and methylphenoxyphosphino. The phosphinyl group may preferably be a phosphinyl group having 2 to 30 carbon atoms, and examples include, for example, phosphinyl, dioctyloxyphosphinyl, and diethoxyphosphinyl. The phosphinyloxy group may preferably be a phosphinyloxy group having 2 to 30 carbon atoms, and examples include, for example, diphenoxyphosphinyloxy and dioctyloxyphosphinyloxy. The phosphinylamino group may preferably be a phosphinylamino group having 2 to 30 carbon atoms, and examples include dimethoxyphosphinylamino and dimethylaminophosphinylamino. The silyl group may preferably be a silyl group having 3 to 30 carbon atoms, and examples include trimethylsilyl, t-butyldimethylsilyl, and phenyldimethylsilyl.

The aforementioned substituents may be further substituted with the aforementioned substituents. Examples of such substituents include an alkylcarbonylaminosulfonyl group, an arylcarbonylaminosulfonyl group, an alkylsulfonylaminocarbonyl group, and an arylsulfonylaminocarbonyl group. Specific examples include methylsulfonylaminocarbonyl, p-methylphenylsulfonylaminocarbonyl, acetylaminosulfonyl, and benzoylaminosulfonyl groups.

Preferred examples of $R^1$ or $R^2$ include a halogen atom, an alkyl group (including straight, branched and cyclic alkyl groups), an aryl group, a heterocyclic group, cyano group, carboxyl group, an alkoxyl group, an aryloxy group, a heterocyclyloxy group, an amino group (including anilino group), an acylamino group, an aminocarbonylamino group, an alkoxycarbonylamino group, an aryloxycarbonylamino group, a sulfamoylamino group, an alkyl- or aryl-sulfonylamino group, an alkylthio group, an arylthio group, a heterocyclylthio group, a sulfamoyl group, a sulfo group, an alkyl- or aryl-sulfonyl group, an acyl group, an alkoxycarbonyl group, a carbamoyl group, and an imido group. More preferred examples are a halogen atom, an alkyl group (including straight, branched and cyclic alkyl groups), an aryl group, a heterocyclic group, carboxyl group, an alkoxyl group, an amino group (including anilino group), an acylamino group, a sulfamoyl group, a sulfo group, a carbamoyl group and an imido group. Still more preferred examples are a halogen atom, a straight, branched or cyclic alkyl group having 1 to 6 carbon atoms, an aryl group having 6 to 10 carbon atoms, a heterocyclic group having 1 to 10 carbon atoms, carboxyl group, and a sulfo group. Particularly preferred examples are bromine atom, iodine atom, methyl group, ethyl group, phenyl group, naphthyl group, thienyl group, furyl group, and pyridyl group. m and n represent an integer of 0 to 3. Two or more $R^1$ or $R^2$ existing when m and n are 2, respectively, may be the same or different. m and n preferably is 0 or 1, most preferably 0.

In the formulas, $R^3$ to $R^6$ are the same or different, and each represent a substituted or unsubstituted alkyl group. This alkyl group has the same meaning as that of the alkyl group explained for $R^1$ and $R^2$, and when it has a substituent, the substituent may be a substituent selected from the aforementioned substituent group. $R^3$ to $R^6$ preferably independently represent an alkyl group having 1 to 20 carbon atoms, more preferably an alkyl group having 1 to 15 carbon atoms in total, still more preferably an alkyl group having 1 to 10 carbon atoms in total, particularly preferably an alkyl group having 1 to 3 carbon atoms in total. Moreover, $R^3$ to $R^6$ preferably independently represent an unsubstituted alkyl group, most preferably methyl group.

$R^7$ and $R^8$ are the same or different, and each represent a substituted or unsubstituted alkyl group. The alkyl group include a straight alkyl group (preferably a straight alkyl group having 1 to 30 carbon atoms), a branched alkyl group (preferably a branched alkyl group having 2 to 30 carbon atoms), and a cyclic alkyl group (it includes one having a tricyclo structure, and may preferably be a cycloalkyl group having 3 to 30 carbon atoms or a bicycloalkyl group having 5 to 30 carbon atoms (monovalent group obtained by eliminating one hydrogen atom from a bicycloalkane having 5 to 30 carbon atoms)). Examples include, methyl, ethyl, n-propyl, isopropyl, t-butyl, n-octyl, eicosyl, 2-ethylhexyl, cyclohexyl, cyclopentyl, 4-n-dodecylcyclohexyl, bicyclo[1,2,2]heptan-2-yl, and bicyclo[2,2,2]octan-3-yl.

Among these, a straight alkyl group having 1 to 20 carbon atoms is preferred, a straight alkyl group having 1 to 10 carbon atoms is more preferred, and a straight alkyl group having 1 to 5 carbon atoms is still more preferred.

When $R^7$ and $R^8$ represent a substituted alkyl group, type, number and position of substituent are not particularly limited.

When $R^7$ and $R^8$ represent a substituted alkyl group, preferred substituents are a halogen atom, carboxyl group, a sulfo group, a phosphate group, an alkylthio group, an arylthio group, and a heterocyclylthio group, more preferred are carboxyl group, a sulfo group, and a phosphate group, and most preferred is a sulfo group.

When $R^7$ and $R^8$ represent a substituted straight alkyl group, the substitution position is preferably a position of such an atom that there should be two or more atoms between the atom and the nitrogen atom on which $R^1$ or $R^2$ substitutes, more preferably a position of an end carbon atom, and the number of the substituent is preferably 1.

$L^1$ to $L^3$ are the same or different, and each represent a substituted or unsubstituted methine group. r is an integer of 0 to 3, and two or more $L^2$ and $L^3$ existing when r is 2 or larger may be the same or different.

When $L^1$ to $L^3$ represent a substituted methine group, the substituent may be a substituent selected from the aforementioned substituent group, and substituents may bond to form a ring.

r represents an integer of 0 to 3, preferably 1 to 3, more preferably 2 or 3, most preferably 3, $L^1$ to $L^3$ preferably include one or more unsubstituted methine groups, and they more preferably consist of 1 to 3 substituted methine groups and unsubstituted methine groups for all the other, most preferably one substituted methine group and unsubstituted methine groups for all the other.

In the formulas, $R^3$ to $R^6$ are the same or different, and each represent a substituted or unsubstituted alkyl group. This alkyl group has the same meaning as that of the alkyl group explained for $R^1$ and $R^2$, and when it has a substituent, the substituent may be a substituent selected from the aforementioned substituent group. $R^3$ to $R^6$ preferably independently represent an alkyl group having 1 to 20 carbon atoms, more preferably an alkyl group having 1 to 15 carbon atoms in total, still more preferably an alkyl group having 1 to 10 carbon atoms in total, particularly preferably an alkyl group having 1 to 3 carbon atoms in total. Moreover, $R^3$ to $R^6$ preferably independently represent an unsubstituted alkyl group, most preferably methyl group.

P and Q each independently represents, $^{123}I$, $^{124}I$, $^{125}I$, $^{131}I$ or $^{18}F$. Among them $^{123}I$, $^{124}I$, $^{125}I$, or $^{131}I$ are preferred, and $^{123}I$, $^{124}I$, or $^{131}I$ are more preferred. M represents hydrogen atom, Na, or K, and preferably represents Na.

The positive charge of the compound represented by the general formula (I) is neutralized with charge of a counter anion existing in the molecule or out of the molecule. Examples of the counter anion include a halogen ion such as chlorine ion, bromine ion and iodine ion, a carboxylate ion such as acetate ion, oxalate ion, fumarate ion and benzoate ion, a sulfonate ion such as p-toluenesulfonate ion, methanesulfonate ion, butanesulfonate ion and benzenesulfonate ion, a sulfate ion, a perchlorate ion, a carbonate ion, a nitrate ion, and the like. When a group having negative charge such as carboxylate group and sulfonate group exists in the molecule, it may form an intramolecular salt with the positive charge of the compound. As the extramolecular counter anion, a halogen ion, a methanesulfonate ion and a sulfate ion are preferred, and chlorine ion, bromine ion and methanesulfonate ion are particularly preferred.

The compound represented by the general formula (I) is more preferably a compound represented by the general formula (II).

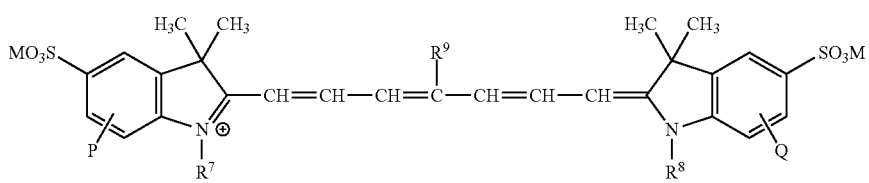

General formula (II)

$R^9$ represents hydrogen atom, a substituted or unsubstituted alkyl group, a substituted or unsubstituted aryl group, a substituted or unsubstituted heterocyclic group, a substituted or unsubstituted acylamino group, a substituted or unsubstituted arylamino group, a substituted or unsubstituted arylthio group, a substituted or unsubstituted aryloxy group, a substituted or unsubstituted carbamoyl group, or a halogen atom. When $R^9$ is a substituted or unsubstituted alkyl group, $R^9$ preferably has 1 to 20 carbon atoms in total, more preferably 1 to 15 carbon atoms in total, still more preferably 1 to 10 carbon atoms in total. Particularly preferred examples include methyl group, ethyl group, n-propyl group, 2-propyl group and cyclopropyl group.

When $R^9$ is a substituted or unsubstituted aryl group, $R^9$ preferably has 5 to 20 carbon atoms in total, more preferably 5 to 15 carbon atoms in total, still more preferably 5 to 10 carbon atoms in total. Particularly preferred examples include phenyl group, 4-methylphenyl group, 4-phenyphenyl group, and naphthyl group.

When $R^9$ is a substituted or unsubstituted heterocyclic group, $R^9$ preferably has 1 to 20 carbon atoms in total, more preferably 1 to 15 carbon atoms in total, still more preferably 1 to 10 carbon atoms in total. Particularly preferred examples include 4-pyridyl group, 2-furyl group, 2-thienyl group, and 2-oxopyrrolidin-1-yl group.

When $R^9$ is a substituted or unsubstituted acylamino group, $R^9$ preferably has 1 to 20 carbon atoms in total, more preferably 1 to 15 carbon atoms in total, still more preferably 1 to 10 carbon atoms in total. Particularly preferred examples include acetylamino group, benzoylamino group, pivaloylamino group, and 4-phenylbenzoylamino group.

When $R^9$ is a substituted or unsubstituted carbamoyl group, $R^9$ preferably has 1 to 20 carbon atoms in total, more preferably 1 to 15 carbon atoms in total, still more preferably 1 to 10 carbon atoms in total. Particularly preferred examples include carbamoyl group, N-methylcarbamoyl group, N-phenylcarbamoyl group and N,N-dimethylcarbamoyl group.

When $R^9$ is a substituted or unsubstituted arylamino group, $R^9$ preferably has 1 to 20 carbon atoms in total, more preferably 1 to 15 carbon atoms in total, still more preferably 1 to 10 carbon atoms in total. Particularly preferred examples include N-phenylamino group, N-tolylamino group, and N,N-diphenylamino group.

When $R^9$ is a substituted or unsubstituted arylthio group, $R^9$ preferably has 1 to 20 carbon atoms in total, more preferably 1 to 15 carbon atoms in total, still more preferably 1 to 10 carbon atoms in total. Particularly preferred examples include phenylthio group, tolylthio group, 4-phenylphenylthio group, and naphthylthio group.

When $R^9$ is a substituted or unsubstituted aryloxy group, $R^9$ preferably has 1 to 20 carbon atoms in total, more preferably 1 to 15 carbon atoms in total, still more preferably 1 to 10 carbon atoms in total. Particularly preferred examples include phenyloxy group, 4-acetylaminophenyloxy group, 4-phenylphenyloxy group, and naphthyloxy group.

Specific examples of the compound of the present invention are shown below. However, the compound of the present invention is not limited to these.

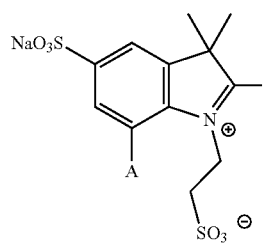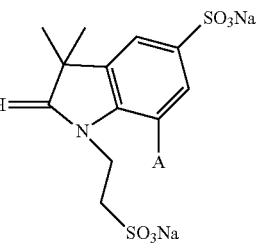

| Compound 1 | A = $^{123}$I |
| Compound 2 | A = $^{124}$I |
| Compound 3 | A = $^{125}$I |
| Compound 4 | A = $^{131}$I |
| Compound 5 | A = $^{18}$F |

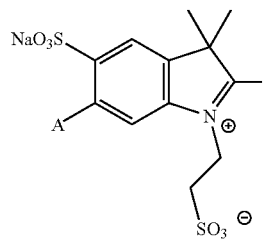

| Compound 6 | A = $^{123}$I |
| Compound 7 | A = $^{124}$I |
| Compound 8 | A = $^{125}$I |
| Compound 9 | A = $^{131}$I |
| Compound 10 | A = $^{18}$F |

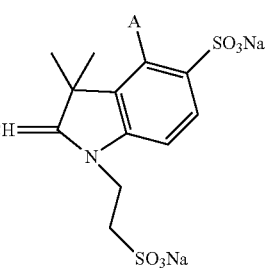

| Compound 11 | A = $^{123}$I |
| Compound 12 | A = $^{124}$I |
| Compound 13 | A = $^{125}$I |
| Compound 14 | A = $^{131}$I |
| Compound 15 | A = $^{18}$F |

-continued
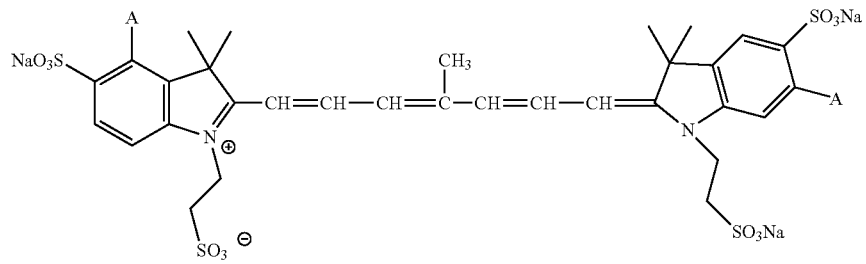
Compound 16  A = $^{123}$I
Compound 17  A = $^{124}$I
Compound 18  A = $^{125}$I
Compound 19  A = $^{131}$I
Compound 20  A = $^{18}$F
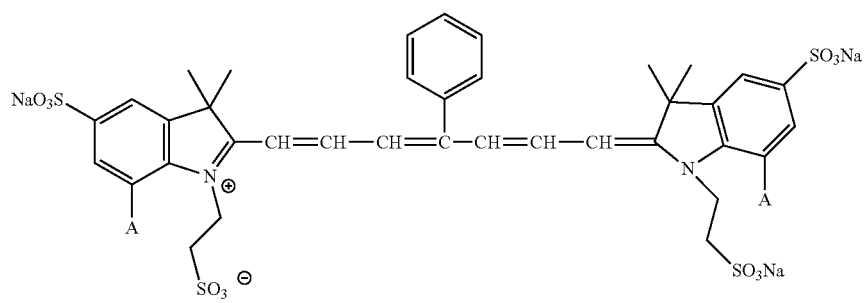
Compound 21  A = $^{123}$I
Compound 22  A = $^{124}$I
Compound 23  A = $^{125}$I
Compound 24  A = $^{131}$I
Compound 25  A = $^{18}$F
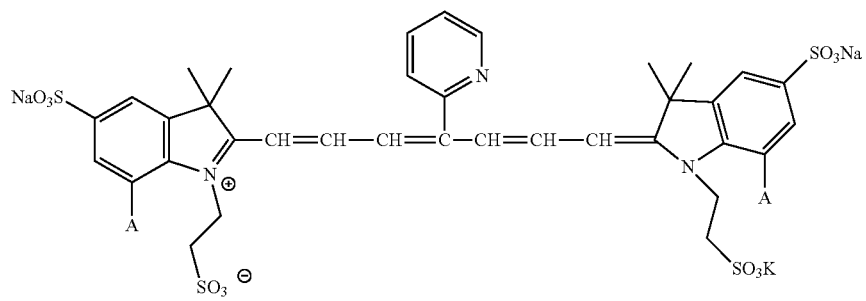
Compound 26  A = $^{123}$I
Compound 27  A = $^{124}$I
Compound 28  A = $^{125}$I
Compound 29  A = $^{131}$I
Compound 30  A = $^{18}$F

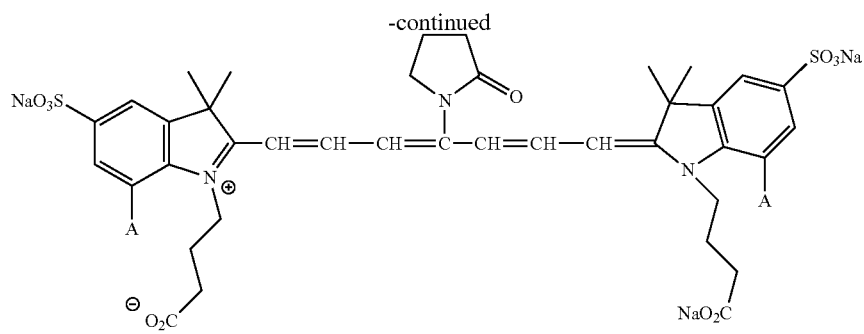
Compound 31  A = $^{123}$I
Compound 32  A = $^{124}$I
Compound 33  A = $^{125}$I
Compound 34  A = $^{131}$I
Compound 35  A = $^{18}$F
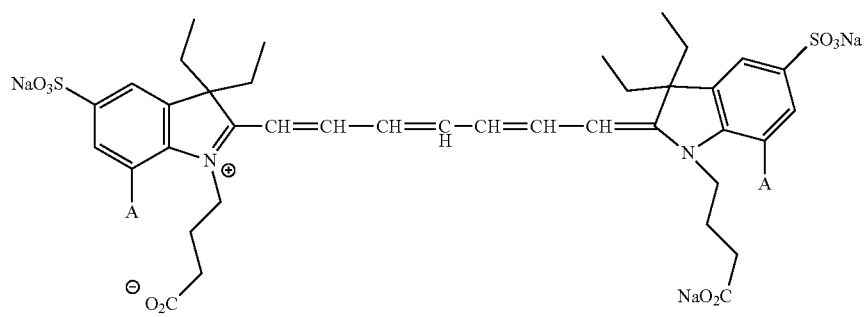
Compound 36  A = $^{123}$I
Compound 37  A = $^{124}$I
Compound 38  A = $^{125}$I
Compound 39  A = $^{131}$I
Compound 40  A = $^{18}$F
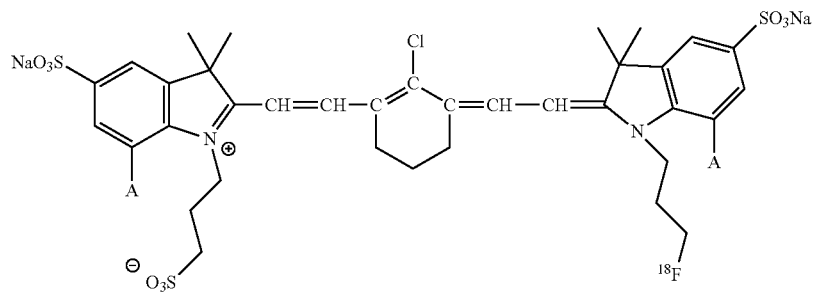
Compound 41  A = $^{123}$I
Compound 42  A = $^{124}$I
Compound 43  A = $^{125}$I
Compound 44  A = $^{131}$I
Compound 45  A = $^{18}$F

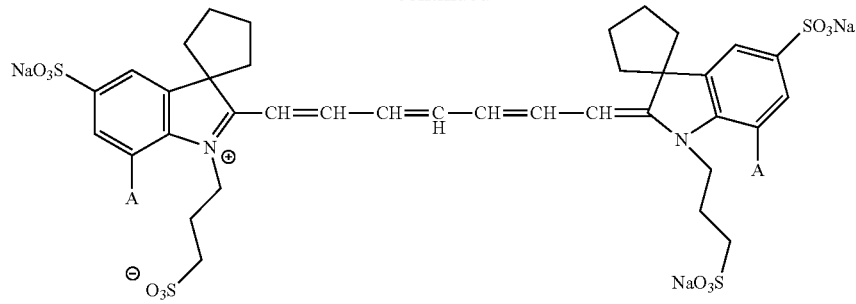
Compound 46  A = $^{123}$I
Compound 47  A = $^{124}$I
Compound 48  A = $^{125}$I
Compound 49  A = $^{131}$I
Compound 50  A = $^{18}$F
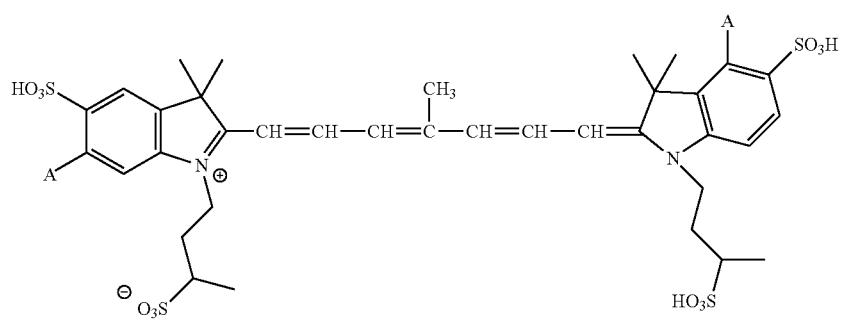
Compound 51  A = $^{123}$I
Compound 52  A = $^{124}$I
Compound 53  A = $^{125}$I
Compound 54  A = $^{131}$I
Compound 55  A = $^{18}$F
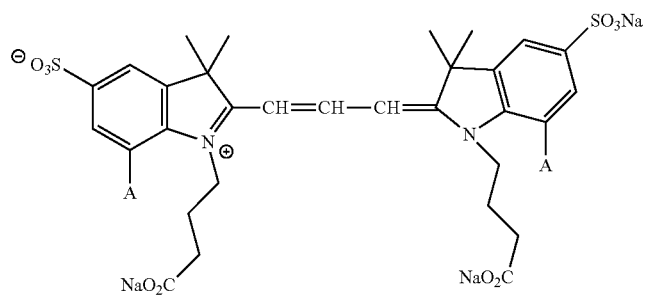
Compound 56  A = $^{123}$I
Compound 57  A = $^{124}$I
Compound 58  A = $^{125}$I
Compound 59  A = $^{131}$I
Compound 60  A = $^{18}$F

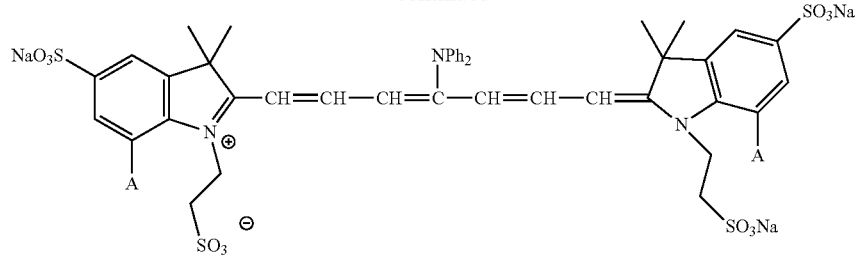
Compound 61  A = $^{123}$I
Compound 62  A = $^{124}$I
Compound 63  A = $^{125}$I
Compound 64  A = $^{131}$I
Compound 65  A = $^{18}$F
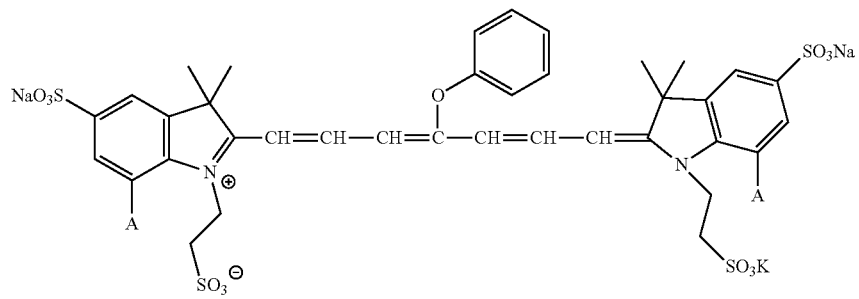
Compound 66  A = $^{123}$I
Compound 67  A = $^{124}$I
Compound 68  A = $^{125}$I
Compound 69  A = $^{131}$I
Compound 70  A = $^{18}$F
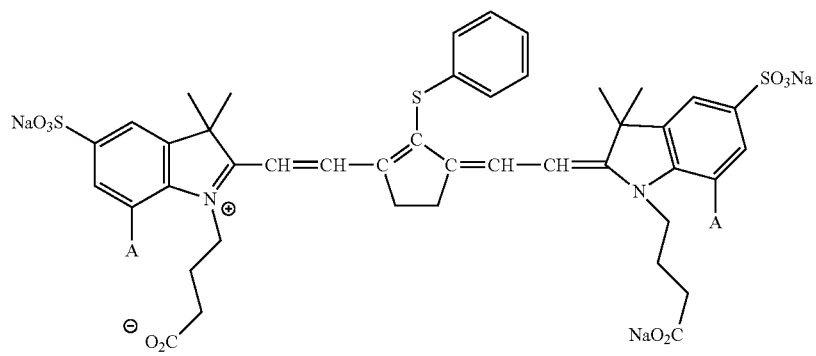
Compound 71  A = $^{123}$I
Compound 72  A = $^{124}$I
Compound 73  A = $^{125}$I
Compound 74  A = $^{131}$I
Compound 75  A = $^{18}$F -continued

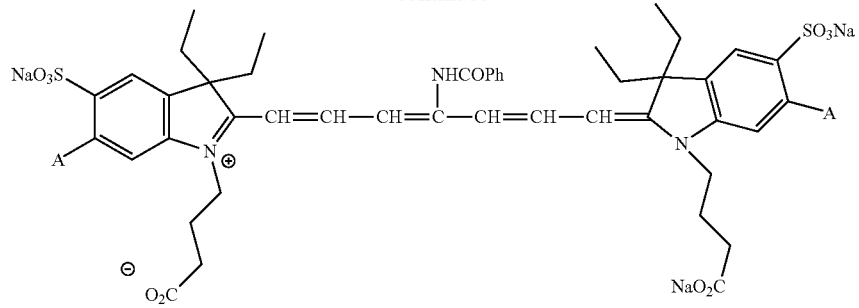

Compound 76   A = $^{123}$I
Compound 77   A = $^{124}$I
Compound 78   A = $^{125}$I
Compound 79   A = $^{131}$I
Compound 80   A = $^{18}$F The compounds represented by the aforementioned general formulas (I) and (II) can be prepared on the basis of, for example, the method for a reaction of a heterocyclic quaternary salt compound and a dianil compound described in Japanese Patent Unexamined Publication (Kokai) No. 2003-160558, the disclosure of which is expressly incorporated herein by reference in its entirety, with introducing a radioactive isotope in any of the stages.

By the various researches of the inventors of the present invention, it was found that the compounds represented by the aforementioned general formulas (I), and (II) can be efficiently prepared by using a heterocyclic quaternary salt compound introduced with a radioactive isotope as the heterocyclic quaternary salt compound used in the method described in Japanese Patent Unexamined Publication No. 2003-160558, the disclosure of which is expressly incorporated herein by reference in its entirety.

As the aforementioned heterocyclic quaternary salt compound introduced with a radioactive isotope, for example, a compound represented the following general formula (III) can be used.

General formula (III)

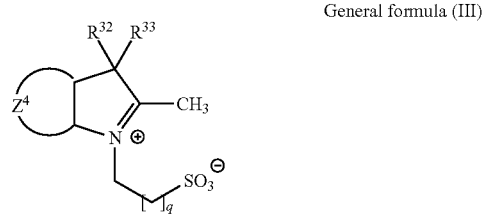

The compound represented by the general formula (III) can be prepared by a reaction of a compound represented by the following general formula (IV):

General formula (IV)

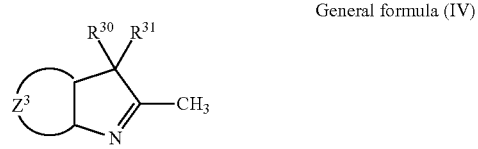

wherein, in the formula, $R^{30}$ and $R^{31}$ are the same or different, and each represent a substituted or unsubstituted alkyl group, and $Z^3$ represents an atomic group forming a condensed benzo ring having one or more substituents selected from the group consisting of iodine and fluorine and one or more substituents selected from the group consisting of sulfo group and sulfo group of which hydrogen atom is replaced with an alkali metal, or a condensed naphtho ring having one or more substituents selected from the group consisting of iodine and fluorine and one or more substituents selected from the group consisting of sulfo group and sulfo group of which hydrogen atom is replaced with an alkali metal, with a halogenated alkylsulfonic acid or the like.

$R^{30}$ and $R^{31}$ more preferably represent an alkyl group having 1 to 15 carbon atoms in total, still more preferably an alkyl group having 1 to 10 carbon atoms in total, particularly preferably an alkyl group having 1 to 3 carbon atoms in total. Moreover, $R^{30}$ and $R^{31}$ preferably independently represent an unsubstituted alkyl group, most preferably methyl group.

As the compound represented by the aforementioned general formula (IV), a compound represented by the following general formula (V) is preferred.

General formula (V)

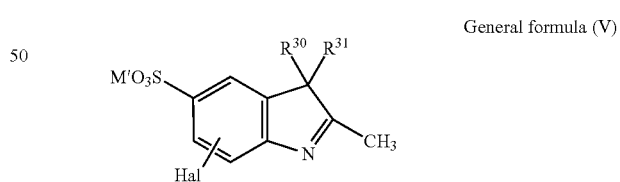

In the formula, Hal represents iodine or fluorine, and M' represents hydrogen atom or an alkali metal atom.

EXAMPLES

Hereafter, the present invention will be still more specifically explained with reference to the following examples. However, the scope of the present invention is not limited by

Example 1

Synthesis of Compound 4

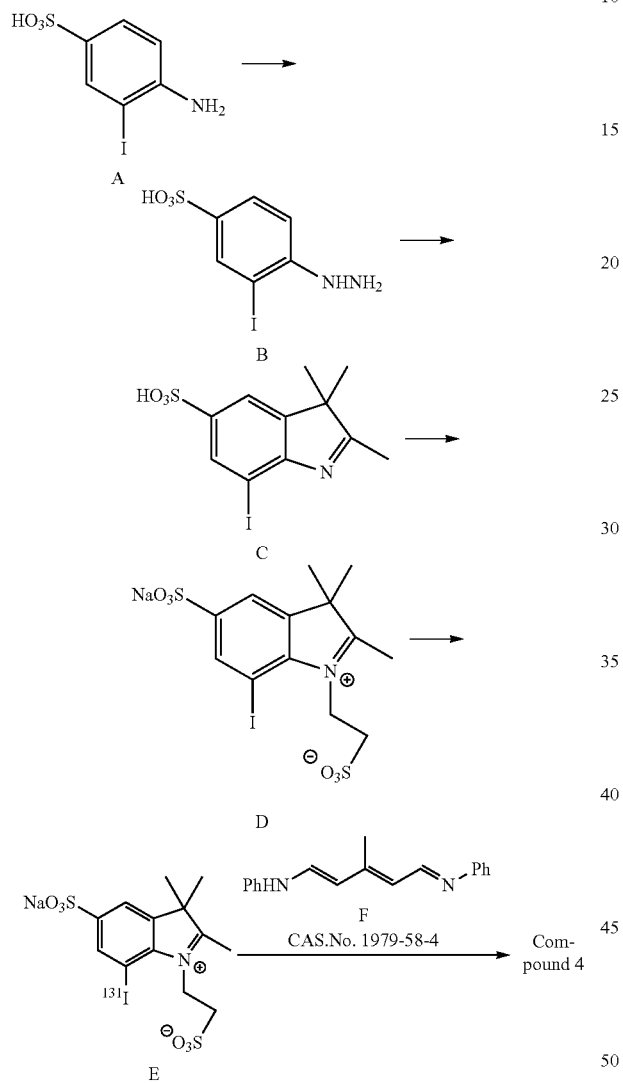

Compound A (CAS. No. 67877-88-7) was diazotized according to the method described in J. Chem. Soc., 95, 1708 (1909), the disclosure of which is expressly incorporated herein by reference in its entirety, and then the resultant was reduced with $SnCl_2$ to obtain Compound B. Compound B was reacted with methyl isopropyl ketone according to the method described in Tetrahedron, 59, 3109 (2003), the disclosure of which is expressly incorporated herein by reference in its entirety, to obtain Compound C. Compound C was reacted with 2-bromoethanesulfonic acid to obtain Compound D ($^1$H NMR δ ($D_2O$): 8.3 (s, 1H), 7.9 (s, 1H), 4.9 (t, 2H, J=6.0 Hz), 3.9 (s, 3H), 3.7 (t, 2H, J=6.0 Hz), 1.6 (s, 6H)). Compound D was converted into Compound E labeled with $^{131}$I according to the method described in Japanese Patent Unexamined Publication No. 1-160923, and the resultant was immediately reacted with Compound F according to the method described in Japanese Patent Unexamined Publication No. 2003-160558 to synthesize Compound 4 (yield of the final step: 65%, labeling ratio: 80%, λ max: 742 nm).

Example 2

Synthesis of Compound 1

Compound 1 was prepared in a similar manner to that of Example 1 except Compound E' labeled with $^{123}$I was used instead of Compound E labeled with $^{131}$I. (yield of the final step: 40%, labeling ratio: 70%, λ max: 741 nm)

Example 3

Synthesis of Compound 9, Compound 14, and Compound 19

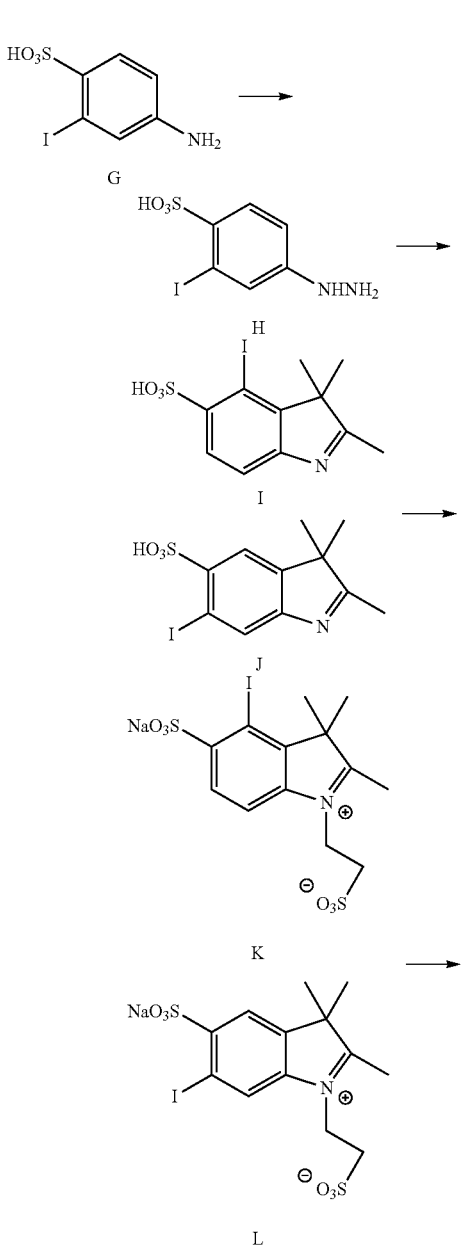

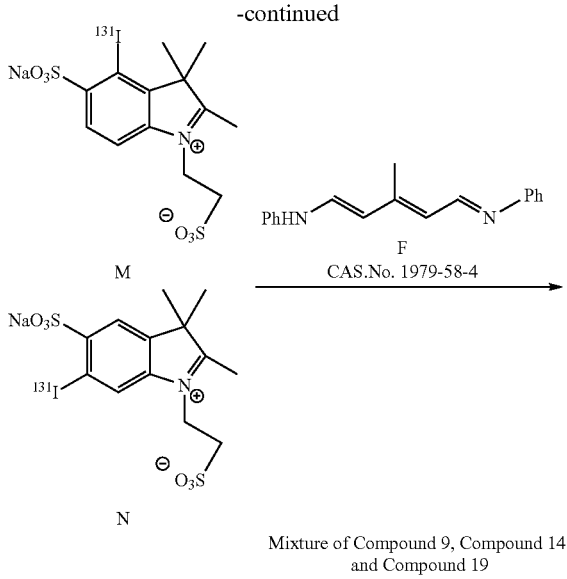

Mixture of Compound 9, Compound 14, and Compound 19

Compound G was synthesized according to the method described in J. Chem. Soc., 99, 333 (1911), the disclosure of which is expressly incorporated herein by reference in its entirety. Thereafter, the synthesis was performed in the same manner as that of the synthesis method of Compound 4, except that since Compound I and Compound J ($^1$H NMR δ (D$_2$O): 7.9 (s: Compound J), 7.8 (s, Compound J), 7.8 (d, J=0.5: Compound I), 7.5 (d, J=0.5, Compound I), 4.9 (t, 2H, J=6.0 Hz), 3.9 (s, 3H), 3.7 (t, 2H, J=6.0 Hz), 1.6 (s, 6H)) were obtained as a mixture of positional isomers in the synthesis thereof, and they could not be separated, they were used as a mixture for the subsequent reactions. Compound 9, Compound 14, and Compound 19 were obtained as a mixture (yield of the dye-forming step: 70%, labeling ratio: 82%, λ max: 746 nm).

Example 4

Synthesis of Compound 6, Compound 11 and Compound 16

Compound 6, Compound 11 and Compound 16 were obtained as a mixture in a similar manner to that of Example 3 except Compound E' labeled with $^{123}$I was used instead of Compound E labeled with $^{131}$I. (yield of the dye-forming step: 52%, labeling ratio: 60%, λ max: 745 nm)

Example 5

Synthesis of Compound 5

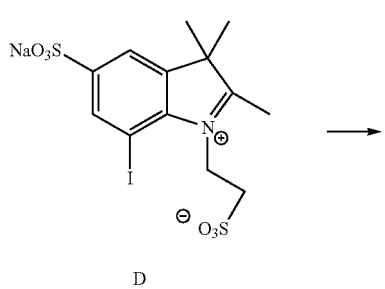

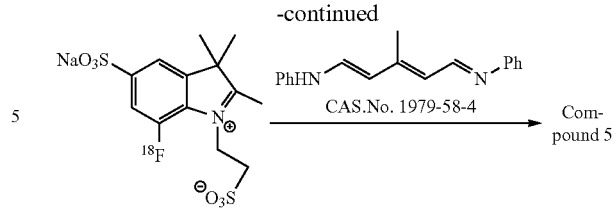

Compound D was reacted with a large excess amount of K$^{18}$F at 100° C. in sulfolane to obtain $^{18}$F-labeled Compound O at a yield of 15%, and this compound was immediately reacted with Compound F according to the method described in Japanese Patent Unexamined Publication No. 2003-160558 to synthesize Compound 5 (yield of the dye-forming step: 60%, labeling ratio: 50%, λ max: 738 nm).

Example 6

Synthesis of Compound 10, Compound 15 and Compound 20

A mixture of Compound 10, Compound 15 and Compound 20 was obtained in the same manner as that of the synthesis of Compound 5 except that a mixture of Compounds K and L was used instead of Compound D (yield of the dye-forming step: 62%, labeling ratio: 45%, λ max: 735 nm).

INDUSTRIAL APPLICABILITY

According to the present invention, there is provided a radioactive isotope-labeled dye compound for which various industrial uses are expected.

What is claimed is:

1. A compound represented by the following general formula (I):

General formula (I)

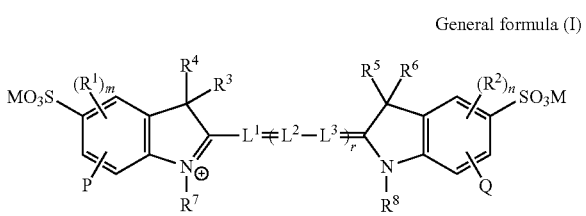

wherein R$^1$ and R$^2$ each independently represent a substituent, R$^3$ to R$^6$ are the same or different, and each represent a substituted or unsubstituted alkyl group; R$^7$ and R$^8$ represent a substituted or unsubstituted alkyl group; L$^1$ to L$^3$ are the same or different, and each represent a substituted or unsubstituted methine group; r represents an integer of 0 to 3; and two or more L$^2$ and L$^3$ existing when r is 2 or larger may be the same or different; P and Q independently represent $^{123}$I, $^{124}$I, $^{125}$I, $^{131}$I or $^{18}$F; M represents hydrogen atom, Na, or K; and m and n independently represent an integer of 0 to 2.

2. The compound according to claim 1, which is represented by the following general formula (II):

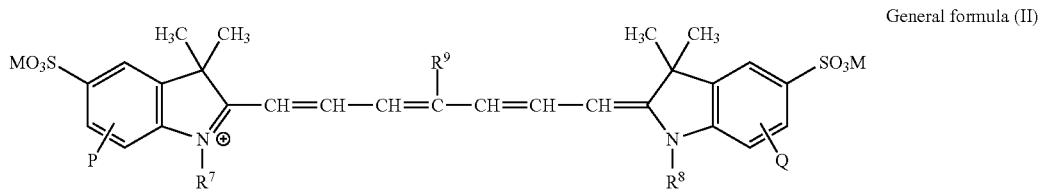

General formula (II)

wherein $R^9$ represents hydrogen atom, a substituted or unsubstituted alkyl group, a substituted or unsubstituted aryl group, a substituted or unsubstituted heterocyclic group, a substituted or unsubstituted acylamino group, a substituted or unsubstituted arylamino group, a substituted or unsubstituted arylthio group, a substituted or unsubstituted aryloxy group, a substituted or unsubstituted carbamoyl group or a halogen atom.

3. A compound represented by any one of the following formulas 1 to 4:

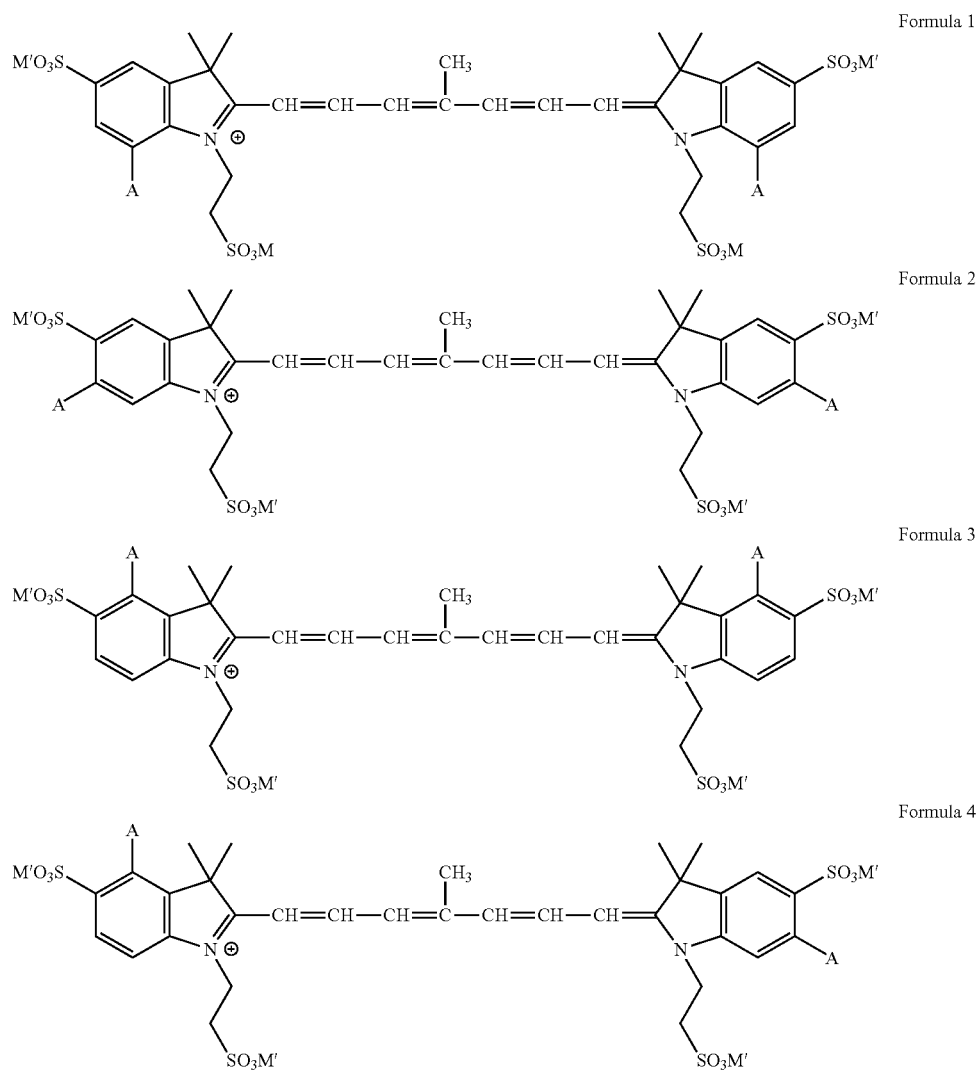

wherein A represents $^{123}I$, $^{124}I$, $^{125}I$, $^{131}I$, or $^{18}F$, and M' represents Na or K.

* * * * *